(12) United States Patent
Divita et al.

(10) Patent No.: US 10,189,876 B2
(45) Date of Patent: *Jan. 29, 2019

(54) CELL PENETRATING PEPTIDES FOR INTRACELLULAR DELIVERY OF MOLECULES

(71) Applicant: AADIGEN, LLC, Pacific Palisades, CA (US)

(72) Inventors: Gilles Divita, Saint-Andre-De-Sangonis (FR); Sebastien Deshayes, Montpellier (FR); Karidia Konate, Montpellier (FR); May Catherine Morris, Mauguio (FR)

(73) Assignee: Aadigen, LLC, Pacific Palisades, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/802,402

(22) Filed: Nov. 2, 2017

(65) Prior Publication Data

US 2018/0179253 A1    Jun. 28, 2018

Related U.S. Application Data

(63) Continuation of application No. 14/433,578, filed as application No. PCT/EP2013/070685 on Oct. 4, 2013, now Pat. No. 9,834,581.

(30) Foreign Application Priority Data

Oct. 4, 2012    (WO) .................. PCT/IB2012/055345

(51) Int. Cl.
| | |
|---|---|
| C07K 7/06 | (2006.01) |
| C07K 7/08 | (2006.01) |
| C07K 14/00 | (2006.01) |
| A61K 31/337 | (2006.01) |
| A61K 31/704 | (2006.01) |
| A61K 47/64 | (2017.01) |
| A61K 47/69 | (2017.01) |
| A61K 47/10 | (2017.01) |

(52) U.S. Cl.
CPC .............. *C07K 7/06* (2013.01); *A61K 31/337* (2013.01); *A61K 31/704* (2013.01); *A61K 47/64* (2017.08); *A61K 47/6929* (2017.08); *C07K 7/08* (2013.01); *C07K 14/001* (2013.01); *A61K 47/10* (2013.01)

(58) Field of Classification Search
CPC ........ A61K 47/64; A61K 48/00; A61K 38/00; A61K 47/42; A61K 49/0056; A61K 47/62; C07K 2319/00; C07K 2319/70
See application file for complete search history.

(56) References Cited

U.S. PATENT DOCUMENTS

| | | | |
|---|---|---|---|
| 7,514,530 B2 | 4/2009 | Divita et al. | |
| 9,376,468 B2 | 6/2016 | Divita et al. | |
| 9,579,395 B2 | 2/2017 | Divita et al. | |
| 9,598,465 B2 | 3/2017 | Divita et al. | |
| 9,834,581 B2 | 12/2017 | Divita et al. | |
| 2016/0145299 A1 | 5/2016 | Divita et al. | |
| 2017/0081661 A1 | 3/2017 | Divita et al. | |
| 2017/0258928 A1 | 9/2017 | Divita et al. | |

FOREIGN PATENT DOCUMENTS

| | | | |
|---|---|---|---|
| EP | 1 795 539 A1 | 6/2005 | |
| FR | 2007069090 A2 * | 6/2007 | ............... C07K 7/06 |
| WO | WO-2007/069090 A2 | 6/2007 | |
| WO | WO-2007/069090 A3 | 6/2007 | |

OTHER PUBLICATIONS

Barre-Sinoussi, F. et al. (May 20, 1983) "Isolation of a T-Lymphotropic Retrovirus from a Patient at Risk for Acquired Immune Deficiency Syndrome (AIDS)," *Science* 220(4599):868-871.
Crombez, L. et al. (2009, e-pub. May 29, 2009). "Targeting Cyclin B1 Through Peptide-Based Delivery of siRNA Prevents Tumor Growth," *Nucleic Acid Research* 37(14):4559-4569.
Crombez, L. et al. (Jan. 2009). "A New Potent Secondary Amphipathic Cell-Penetrating Peptide for siRNA Delivery Into Mammalian Cells," *Mol. Ther.* 17(1):95-103.
Deshayes, S. et al. (2005). "Cell-penetrating Peptides: Tools for Intracellular Delivery of Therapeutics," *Cell Mol Life Sci.* 62:1839-1849.
Deshayes, S. et al. (2008, e-pub. Oct. 25, 2007). "Delivery of Proteins and Nucleic Using a Non-Covalent Peptide-Based Strategy," *Adv. Drug Deliv. Rev.* 60:537-547.
Glover, D.J. et al. (Apr. 2005, e-pub. Mar. 10, 2005). "Towards Safe, Non-Viral Therapeutic Gene Expression in Humans," *Nat. Rev. Genet.* 6:299-310.
Heitz, F. et al. (2009). "Themed Section: Vector Design and Drug Delivery Review. Twenty Years of Cell-Penetrating Peptides: From Molecular Mechanisms to Therapeutics," *British Journal of Pharmacology* 157:195-206.
Kurzawa, L. et al. (2010, e-pub. Feb. 25, 2010). "PEP and CADY-mediated 1-23 delivery of fluorescent peptides and proteins into living cells," *Biochimica Et Biophysica Acta* 1798(12):2274-2285.
Mery, J. et al. (Jul./Aug. 1992). "Disulfide Bond as Peptide-Resin Linkage in Boc-Bzl SPPS, for Potential Biochemical Applications," *Pept Res.* 5(4):233-40.

(Continued)

*Primary Examiner* — Marcela M Cordero Garcia
*Assistant Examiner* — Jia-Hai Lee
(74) *Attorney, Agent, or Firm* — Morrison & Foerster LLP

(57) ABSTRACT

A cell-penetrating peptide characterized in that it comprises an amino acid sequence consisting of XWXRLXXXXXX (SEQ ID No: 5), wherein X in position 1 is beta-A or S; X in positions 3, 9 and 10 are, independently from each other, W or F; X in position 6 is R if X in position 8 is S, and X in position 6 is S if X in position 8 is R; X in position 7 is L or none; X in position 11 is R or none, and wherein X in position 7 is L if X in position 11 is none.

16 Claims, 6 Drawing Sheets

Specification includes a Sequence Listing.

(56) References Cited

OTHER PUBLICATIONS

Morris, M.C. et al. (1997). "A New Peptide Vector for Efficient Delivery of Oligonucleotides Into Mammalian Cells," *Nucleic Acids Res.* 25(14):2730-2736.

Morris, M.C. et al. (Dec. 2001). "A Peptide Carrier for the Delivery of Biologically Active Proteins Into Mammalian Cells," *Nat. Biotechnol.* 19:1173-1176.

Morris et al. (2007, e-pub. Mar. 5, 2007) "A Non-Covalent Peptide-Based Carrier for in vivo Delivery of DNA Mimics," *Nucleic Acids Research* 35(7):e49.

Roisin, A. et al. (Mar. 5, 2004—e-pub. Dec. 10, 2003) "Inhibition of HIV-1 replication by cell-penetrating peptides binding Rev." *J. Biol. Chem.* 279(10):9208-14.

Verdine, G.L. et al. (2012). "Stapled peptides for Intracellular Drug Targets," Chapter 1 in *Methods and Enzymology*, 503:3-33.

Whitehead, K.A. et al. (Feb. 2009). "Knocking Down Barriers: Advances in siRNA Delivery," *Nat Rev Drug Discov.* 8:129-138.

International Search Report issued in corresponding International Patent Application No. PCT/EP2013/070685 dated Dec. 12, 2013.

U.S. Appl. No. 15/539,619, internationally filed Dec. 23, 2015, by Divita et al. (Copy not attached).

U.S. Appl. No. 15/463,994, filed Mar. 20, 2017, by Divita et al. (Copy not attached).

* cited by examiner

CELL PENETRATING PEPTIDES FOR INTRACELLULAR DELIVERY OF MOLECULES

CROSS REFERENCE TO RELATED APPLICATIONS

This patent application is a continuation application of U.S. patent application Ser. No. 14/433,578, with the International Filing Date of Oct. 4, 2013, which is a National Phase application under 35 U.S.C. § 371 of International Application No. PCT/EP2013/070685 filed Oct. 4, 2013, which claims priority to PCT/IB2012/055345, filed Oct. 4, 2012, the disclosure of each which is hereby incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 737372000601SeqList.txt, date recorded: Nov. 2, 2017, size: 25 KB).

FIELD OF THE INVENTION

The present invention pertains to the field of intracellular delivery of molecules such as nucleic acids and small hydrophobic molecules. In particular, the invention relates to a new cell-penetrating peptide (CPP) family, which exhibits a high efficacy and a low toxicity.

BACKGROUND OF THE INVENTION

Although small molecules remain the major drugs used in clinic, in numerous cases, their therapeutic impact has reached limitations such as insufficient capability to reach targets, lack of specificity, requirement for high doses leading to toxicity and major side effects. Over the past ten years, in order to circumvent limitations of small molecules and of gene-based therapies, we have witnessed a dramatic acceleration in the discovery of larger therapeutic molecules such as proteins, peptides and nucleic acids which present a high specificity for their target but do not follow Lipinski's rules. Pharmaceutical potency of these molecules remains restricted by their poor stability in vivo and by their low uptake in cells. Therefore, "delivery" has become a central piece of the therapeutic puzzle and new milestones have been established to validate delivery strategies: (a) lack of toxicity, (b) efficiency at low doses in vivo, (c) easy to handle for therapeutic applications (d) rapid endosomal release and (e) ability to reach the target. Although viral delivery strategies had given much hope for gene and cellular therapies, their clinical application has suffered from side- and toxicity-effects [1,2]. Researches were mainly focused on the development of non-viral strategies, and different methods have been proposed including lipid, polycationic nanoparticles and peptide-based formulations, but only few of these technologies have been efficient in vivo and have reached the clinic. Cell Penetrating Peptides (CPP) are one of the most promising non-viral strategies. Although definition of CPPs is constantly evolving, they are generally described as short peptides of less than 30 amino acids either derived from proteins or from chimeric sequences. They are usually amphipathic and possess a net positive charge [3-5]. CPPs are able to penetrate biological membranes, to trigger the movement of various biomolecules across cell membranes into the cytoplasm and to improve their intracellular routing, thereby facilitating interactions with the target. CPPs can be subdivided into two main classes, the first requiring chemical linkage with the cargo and the second involving the formation of stable, non-covalent complexes. CPPs from both strategies have been reported to favour the delivery of a large panel of cargos (plasmid DNA, oligonucleotide, siRNA, PNA, protein, peptide, liposome, nanoparticle . . . ) into a wide variety of cell types and in vivo models [3-7].

Twenty years ago, the concept of protein transduction domain (PTD) was proposed based on the observation that some proteins, mainly transcription factors, could shuttle within cells and from one cell to another [for review see ref 3,4]. The first observation was made in 1988, by Frankel and Pabo. They showed that the transcription-transactivating (Tat) protein of HIV-1 could enter cells and translocate into the nucleus. In 1991, the group of Prochiantz reached the same conclusions with the Drosophila Antennapedia homeodomain and demonstrated that this domain was internalized by neuronal cells. These works were at the origin of the discovery in 1994 of the first Protein Transduction Domain: a 16 mer-peptide derived from the third helix of the homeodomain of Antennapedia named Penetratin. In 1997, the group of Lebleu identified the minimal sequence of Tat required for cellular uptake and the first proofs-of-concept of the application of PTD in vivo, were reported by the group of Dowdy, for the delivery of small peptides and large proteins. Historically, the notion of Cell Penetrating Peptide (CPP) was introduced by the group of Langel, in 1998, with the design of the first chimeric peptide carrier, the Transportan, which derived from the N-terminal fragment of the neuropeptide galanin, linked to mastoparan, a wasp venom peptide. Transportan has been originally reported to improve the delivery of PNAs both in cultured cells and in vivo. In 1997, the group of Heitz and Divita proposed a new strategy involving CPP in the formation of stable but non-covalent complexes with their cargo [7]. The strategy was first based on the short peptide carrier (MPG) consisting of two domains: a hydrophilic (polar) domain and a hydrophobic (apolar) domain. MPG was designed for the delivery of nucleic acids [7]. The primary amphipathic peptide Pep-1 was then proposed for non-covalent delivery of proteins and peptides [8]. Then the groups of Wender and of Futaki demonstrated that polyarginine sequences (Arg8) are sufficient to drive small and large molecules into cells and in vivo. Ever since, many CPPs derived from natural or unnatural sequences have been identified and the list is constantly increasing. Peptides have been derived from VP22 protein of Herpes Simplex Virus, from calcitonin, from antimicrobial or toxin peptides, from proteins involved in cell cycle regulation, as well as from polyproline-rich peptides [reviews 4-6].

DETAILED DESCRIPTION

Figure 1A:
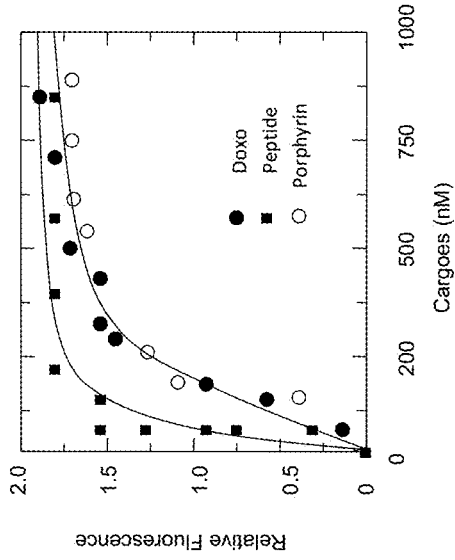
FIGS. 1A-1D show the binding of VEPEP-3i (1A), Short 3 (1B), VEPEP-3J (1C) and Short 4 (1D) peptides with various fluorescently labelled cargoes (as determined by fluorescence spectroscopy).
Figure 1B:
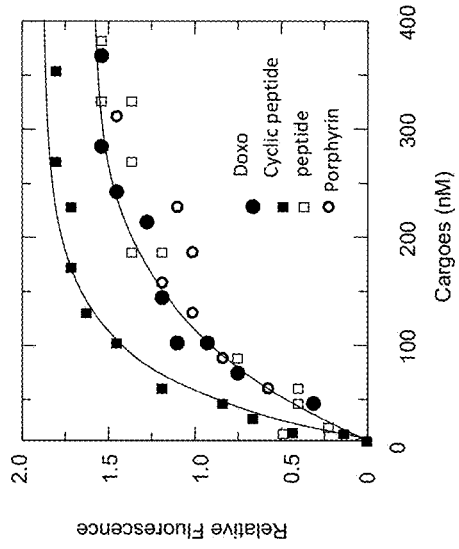
Figure 1C:
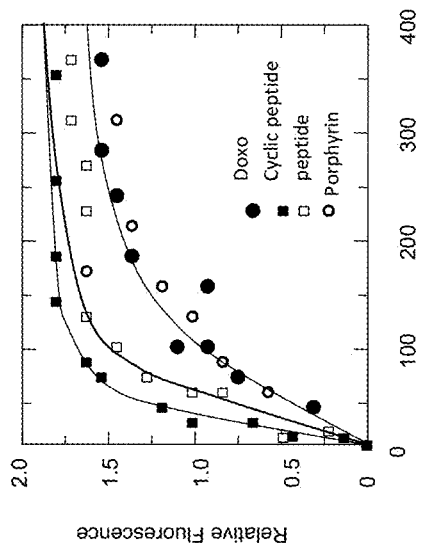
Figure 1D:
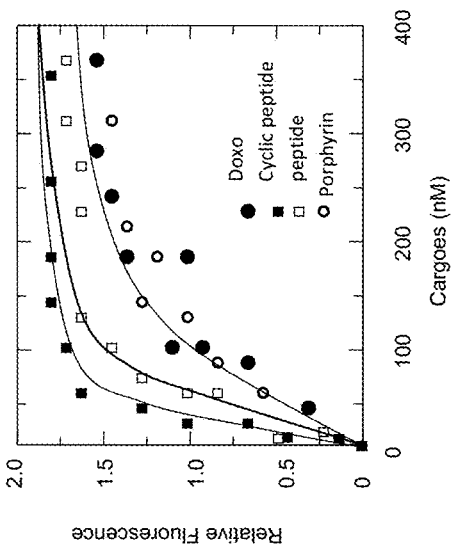

The inventors have now designed a new family of cell-penetrating peptides for the delivery of peptides/proteins and hydrophobic molecules, named VEPEP-4. Delivery strategies using VEPEP-4 peptides as the outer layer of nanoparticles are referred to as NANOPEP-4.

VEPEP-4 are short primary peptides forming stable nanoparticles with molecules such as peptides, peptide-analogues, PNAs and small hydrophobic molecules, hereafter designated as "SHM". VEPEP-4 vectors comprise the following amino acid sequence: XWXRLXXXXXX (SEQ ID No: 5), wherein:

X in position 1 is beta-A or S;

X in positions 3, 9 and 10 are, independently from each other, W or F;

X in position 6 is R if X in position 8 is S, and X in position 6 is S if X in position 8 is R;

X in position 7 is L or none;

X in position 11 is R or none, and wherein X in position 7 is L if X in position 11 is none.

Non-limitative examples of VEPEP-4 peptides according to the present invention comprise an amino acid sequence selected from the group consisting of:

```
X1WWRLSLRWW                (SEQ ID No: 1)

X1WFRLSLRFWR               (SEQ ID No: 2)

X1WWRLRSWFR,               (SEQ ID No: 3)
and

X1WFRLSLRFW,               (SEQ ID No: 4)
``` wherein X1 is beta-A or S.

The present invention also pertains to a stapled cell-penetrating peptide derived from a VEPEP-4 cell-penetrating peptide as described above. A "stapled" peptide designates a peptide which comprises a chemical linkage (in addition to the amino acid chain) between two residues. In a particular embodiment of stapled VEPEP-4 peptides, the VEPEP-4 peptide comprises a hydrocarbon linkage between two residues which are separated by three or six residues. The skilled artisan can obtain these peptides by using techniques which are available in the art, for example as described by Verdine and Hilinski, Methods in Enzymology, 2012 [12].

VEPEP-4 strategy improves both ex-vivo and in vivo delivery and efficiency of peptide/protein/peptide analogue and small hydrophobic molecules, without activating the innate immune response or inducing toxic side effects.

According to a preferred embodiment, a cell-penetrating peptide of the present invention further comprises, covalently linked to the N-terminal end of the amino acid sequence, one or several chemical entities selected in the group consisting of an acetyl, a fatty acid, a cholesterol, a poly-ethylene glycol, a nuclear localization signal, a nuclear export signal, an antibody, a polysaccharide and a targeting molecule (peptide, fatty acid, saccharide).

In particular, PEGylation of VEPEP-4 peptides is advantageous for stabilizing nanoparticles in vivo.

In addition or alternatively, a cell-penetrating peptide according to the invention can comprise, covalently linked to the C-terminal end of its amino acid sequence, one or several groups selected in the group consisting of a cysteamide, a cysteine, a thiol, an amide, a nitrilotriacetic acid optionally substituted, a carboxyl, a linear or ramified C1-C6 alkyl optionally substituted, a primary or secondary amine, an osidic derivative, a lipid, a phospholipid, a fatty acid, a cholesterol, a poly-ethylene glycol, a nuclear localization signal, nuclear export signal, an antibody, a polysaccharide and a targeting molecule.

Another aspect of the present invention is a complex comprising a cell-penetrating peptide as described above and a cargo selected amongst protein/peptide and hydrophobic molecules. Examples of polypeptide cargoes are small peptide or protein, cyclic peptide, peptide-based biomarker, bio-drug, PNA or uncharged oligonucleotides. In a preferred embodiment of the complex according to the invention, the cargo is a small molecule (size lower than 1.5 kDa), either hydrophobic or charged. Preferred cargos in the complexes according to the present invention are anticancer and antiviral drugs, as well as cosmetic agents. Non-limitative examples of small hydrophobic molecules which can be used include amino acids, di- or tri-peptides (labelled or not) daunomycin, Paclitaxel, doxorubicin, AZT, porphyrin, fluorescently-labelled-nucleosides or nucleotides (FAM-Guanosine, CY5_UTP, CY3-UTP), hydrophobic maghemite (contrast agents or magnetic nanoparticles $Fe_2O_3$) and fluorescent dyes.

The size of the complexes described above is preferably between 50 and 200 nm (the size of the complex herein designates its mean diameter).

In the complexes according to the invention, the cargo/VEPEP-4 molar ratio depends on the nature and size of the cargo, but is generally comprised between 1/1 and 1/50. For small peptide cargoes, the cargo/VEPEP-4 molar ratio preferably ranges from 1/5 to 1/20. For small molecule cargoes, the cargo/VEPEP-4 molar ratio preferably ranges from 1/3 to 1/10.

According to an advantageous embodiment of the complexes as described above, the VEPEP-4 peptides comprise a polyethylene glycol group or an acetyl group covalently linked to their N-terminus, and/or a cysteamide group covalently linked to their C-terminus.

The above complexes can be advantageously used as "core shells" for obtaining bigger complexes, or nanoparticles, by an additional step of coating the cargo/VEPEP-4 complex with another layer of cell-penetrating peptides, which can be identical to or different from the VEPEP-4 peptides described above. Examples of such nanoparticles are VEPEP-4/CADY (wherein CADY is a CPP as described in EP1795539 and in [11]), VEPEP-4/PEP-1 (wherein Pep-1 is a CPP as described in [8]), VEPEP-4/MPG (wherein MPG is a CPP as described in U.S. Pat. No. 7,514,530 and in [7, 10]), as well as nanoparticles with an outer layer made of a CPP belonging to another VEPEP family, for example selected from the following list:

```
VEPEP-3a:
                                        (SEQ ID No: 13)
Ac-X₁KWFERWFREWPRKRR-cysteamide VEPEP-3b:
                                        (SEQ ID No: 14)
Ac-X₁KWWERWWREWPRKRK-cysteamide VEPEP-3c:
                                        (SEQ ID No: 15)
Ac-X₁RWWEKWWTRWPRKRK-cysteamide, VEPEP-3d:
                                        (SEQ ID No: 16)
Ac-X₁RWYEKWYTEFPRRRR-cysteamide, VEPEP-3e:
                                        (SEQ ID No: 17)
Ac-X₁RWWRLWWRSWFRLWRR-cysteamide VEPEP-3f:
                                        (SEQ ID No: 18)
Ac-X₁LWWRRWWSRWWPRWRR-cysteamide VEPEP-3g:
                                        (SEQ ID No: 19)
Ac-X₁LWWSRWWRSWFRLWFR-cysteamide, VEPEP-3h:
                                        (SEQ ID No: 20)
Ac-X₁KFWSRFWRSWFRLWRR-cysteamide, VEPEP-6a:
                                        (SEQ ID No: 21)
Ac-X₁LFRALWRLLRSLWRLLWK-cysteamide VEPEP-6b:
                                        (SEQ ID No: 22)
Ac-X₁LWRALWRLWRSLWRLLWKA-cysteamide VEPEP-6c:
                                        (SEQ ID No: 23)
Ac-X₁LWRALWRLLRSLWRLWRKA-cysteamide VEPEP-6d:
                                        (SEQ ID No: 24)
Ac-X₁LWRALWRLWRSLWRLWRKA-cysteamide VEPEP-6e:
                                        (SEQ ID No: 25)
Ac-X₁LWRALWRLLRALWRLLWKA-cysteamide VEPEP-6f:
                                        (SEQ ID No: 26)
Ac-X₁LWRALWRLLRNLWRLLWKA-cysteamide VEPEP-9a1:
                                        (SEQ ID No: 27)
Ac-X₁LRWWLRWASRWFSRWAWWR-cysteamide VEPEP-9a2:
                                        (SEQ ID No: 28)
Ac-X₁LRWWLRWASRWASRWAWFR-cysteamide VEPEP-9b1:
                                        (SEQ ID No: 29)
Ac-X₁RWWLRWASRWALSWRWWR-cysteamide VEPEP-9b2:
                                        (SEQ ID No: 30)
Ac-X₁RWWLRWASRWFLSWRWWR-cysteamide VEPEP-9c1:
                                        (SEQ ID No: 31)
Ac-X₁RWWLRWAPRWFPSWRWWR-cysteamide VEPEP-9c2:
                                        (SEQ ID No: 32)
Ac-X₁RWWLRWASRWAPSWRWWR-cysteamide VEPEP-9d:
                                        (SEQ ID No: 33)
Ac-X₁WWRWWASWARSWWR-cysteamide VEPEP-9e:
                                        (SEQ ID No: 34)
Ac-X₁WWGSWATPRRRWWR-cysteamide VEPEP-9f:
                                        (SEQ ID No: 35)
Ac-X₁ₙWRWWAPWARSWWR-cysteamide VEPEP-3bstapl:
                                        (SEQ ID No: 36)
Ac-X₁KR_SWWERWWR_SSWPRKRK-cysteamide VEPEP-3estapl:
                                        (SEQ ID No: 37)
Ac-X₁RWWR_SLWWRSWS_SRLWRR-cysteamide ST-VEPEP-6a:
                                        (SEQ ID No: 38)
Ac-X₁LFRALWR_SLLRS_SLWRLLWK-cysteamide ST-VEPEP-6aa:
                                        (SEQ ID No: 39)
Ac-X₁LFLARWR_SLLRS_SLWRLLWK-cysteamide ST-VEPEP-6ab:
                                        (SEQ ID No: 40)
Ac-X₁LFRALWS_SLLRS_SLWRLLWK-cysteamide ST-VEPEP-6ad:
                                        (SEQ ID No: 41)
Ac-X₁LFLARWS_SLLRS_SLWRLLWK-cysteamide ST-VEPEP-6b:
                                        (SEQ ID No: 42)
Ac-X₁LFRALWRLLR_SSLWS_SLLWK-cysteamide ST-VEPEP-6ba:
                                        (SEQ ID No: 43)
Ac-X₁LFLARWRLLR_SSLWS_SLLWK-cysteamide ST-VEPEP-6bb:
                                        (SEQ ID No: 44)
Ac-X₁LFRALWRLLS_SSLWS_SLLWK-cysteamide ST-VEPEP-6bd:
                                        (SEQ ID No: 45)
Ac-X₁LFLARWRLLS_SSLWS_SLLWK-cysteamide ST-VEPEP-6c:
                                        (SEQ ID No: 46)
Ac-X₁LFAR_SLWRLLRS_SLWRLLWK-cysteamide,
``` as well as variants thereof (regarding the amino acid sequence and/or the N- and C-terminal chemical groups), wherein $X_1$ is beta-A or S and wherein the residues followed by an inferior "s" are linked by a hydrocarbon linkage. Preferred variants of the above sequences for forming nanoparticles according to the invention are PEGylated at their N-terminal extremity instead of being acetylated.

Another aspect of the present invention pertains to nanoparticles made of a "core shell" comprising a cargo and a first carrier molecule, surrounded by VEPEP-4 peptides. These are herein referred to as "NANOPEP-4" particles. NANOPEP-4 technology constitutes a "custom-built" delivery system containing a common core particle, trapping therapeutic molecule, with surface VEPEP-4 peptides which are preferably functionalized for tumour or tissue targeting in vivo. From a structural point of view, NANOPEP-4 particles are constituted by a "core" which is coated by a layer of VEPEP-4 peptides. The "core" corresponds to a complex comprising a cargo and a vector or carrier such as a first cell-penetrating peptide, a liposome, a polycationic structure, a carbon nanoparticle, etc. In NANOPEP-4 particles, the layer of VEPEP-4 peptides (peripheral peptide) stabilizes the particle and can be functionalized. Functionalizing NANOPEP-4 particle surface with either cholesterol, lipid, PEG-molecules improves particles stability in vivo, favours their administration by either systemic or topical route and allows rapid liberation of active cargoes within tumor cells or tissues. Functionalization of the surface of NANOPEP-4 particles with small FAB fragments, peptides, antibodies and lipids has been shown to favour in vivo tissue or tumor targeting. Also, Functionalizing NANOPEP-4 particle surface with polysaccharide such as PLGA, can be used as formulation for slow release of drug and cargo and allow a long term response in vivo. N-terminal PEGylation of at least part of the VEPEP-4 peptides surrounding the NANOPEP-4 particles increases the biodistribution of cargoes in the tumour, probably by stabilizing the NANOPEP-4 particles in the plasma.

NANOPEP-4 technology improves both cellular and in vivo delivery of biologically active cargoes and has been validated on a large set of cell lines including adherent and suspension cell lines, hard to transfect cell lines. NANOPEP-4 particles strongly interact with cell membranes and enter the cell independently of the endosomal pathway or rapidly escape from early endosomes. NANOPEP-4 technology presents several advantages including rapid delivery with very high efficiency, stability in physiological buffers, protection of the cargo against degradation, lack of toxicity and of sensitivity to serum, ability of forming mix nanoparticles, can be functionalized can be applied to the delivery of different types of cargoes into a large variety of cell lines as well as in animal models, thereby constituting powerful tools for basic research and therapeutic applications. NANOPEP-4 technology can be applied both at therapeutic and diagnostic/theragnostic levels, as well as for imaging.

In a particular embodiment of NANOPEP-4 particles according to the present invention, the cargo is complexed to a first cell-penetrating peptide, which can be, for example, selected amongst CADY, MPG, PEP-1, PPTG1, poly Arginine motif, VEPEP-family peptide (VEPEP-3, VEPEP-4, VEPEP-6, VEPEP-9, stapled or not) as described above (such as SEQ ID Nos: 1 to 5 and 13 to 46 and variants thereof), or any other known CPP. This cargo/CPP complex is then coated with a layer of VEPEP-4 peptides. According to this embodiment, the skilled artisan will advantageously choose the first CPP depending on the nature of the cargo, so that the complex of cargo and first CPP is stable. Hence, a wide diversity of cargoes can be included in NANOPEP-4 particles.

In the nanoparticles as above-described, the core/VEPEP-4 molar ratio depends on the nature and size of the core, but is generally comprised between 1/1 and 1/50. For small peptide/CPP cores, the core/peripheral VEPEP-4 molar ratio preferably ranges from 1/5 to 1/30, depending on the nature of peptide cargo (hydrophobicity and charge).

In a preferred embodiment of the nanoparticles according to the invention, the size of the nanoparticle is between 20 and 300 nm.

According to an advantageous embodiment of the NANOPEP-4 particles according to the invention, the VEPEP-4 peptides forming the peripheral layer of the nanoparticles comprise a poly-ethylene glycol or an acetyl group covalently linked to their N-terminus, and/or a cysteamide group covalently linked to their C-terminus.

According to another preferred embodiment, the core shell of the particles is coated with a VEPEP-4 peptide functionalized with NTA (for example, a VEPEP-4 peptide with nitrilotriacetic acid covalently linked to its C-terminus). This allows the subsequent attachment to the surface of the particle, of any protein (or other molecule) harboring a histidine tag. This strategy offers the major advantage of having a common two-layers particles "NANOPEPHIS-4" which can be associated to any His-tagged molecule.

In particular embodiments of the complexes and nanoparticles according to the invention, at least part of the VEPEP-4 cell-penetrating peptides are bound to a targeting molecule. In the case of NANOPEP-4 particles, at least part of the cell-penetrating peptides which are at the periphery of the nanoparticle are preferentially bound to a targeting molecule. Examples of targeting molecules include antibodies, nanobodies and Fc or FAB fragments (for example targeting HEK2/MUC1/EGF/XCCR4), ligands, especially targeting receptors which are over-expressed at the surface of certain cell-types and homing peptides specific of selected organs. Non-limitative examples of such ligands and homing peptides are: RGD-peptide, homing targeting peptides (brain NT1 peptide, Ganglion GM1 peptide, as well as all other previously described peptides for tissues and cell line targeting), folic acid, polysaccharides, and matrix metalloprotease targeting peptide motif (MMP-9 or MMP3 for tumour selectivity).

According to a particular embodiment of the present invention, the complexes or nanoparticles are formulated se that they can be stored during several months without losing their stability and functional efficacy. In particular, the complexes and nanoparticles of the invention can advantageously be lyophilized in the presence of a sugar. Non-limitative examples of sugars which can be used to that aim are sucrose, glucose, manitol and a mix thereof, and they can be used, for example, in a concentration ranging from 5% to 20%, preferably 5% to 10%, it being understood that a concentration of 5% is obtained by adding 5 grams per liter of solution before lyophilization.

Another aspect of the present invention is the use of a complex or nanoparticle as above-described, as a medicament and as a marker or an imaging agent.

The present invention also pertains to a therapeutic, cosmetic or diagnostic composition comprising a complex or a nanoparticle as described above. For example, a composition comprising a complex or nanoparticle having a peptide targeting protein/protein interactions, involving essential protein CDK and Cyclin required for cell cycle progression as a cargo, and a targeting molecule specific for tumour cells (for example: RGD-peptide, folic acid, MUC-1 or HEK2 antibodies or nanobodies), is part of the present invention. Depending on the application, this composition can be formulated for intravenous, intratumoral, topical, intrarectal, intranasal, transdermal, or intradermal administration, or for administration via a mouth spray, or for administration as a subcutaneous implant for slow release of a drug.

The present invention also pertains to a method for delivering a molecule into a cell in vitro, comprising a step of putting said cell into contact with a complex or nanoparticle as described above.

One of the major advantages of using short peptides with a size of 10 and less residues is the lack of innate immune response associated thereto. Short peptides do not induce allergic response and therefore can be administered by trans-dermal route and topically without any risk of inflammatory response, in contrast to longer peptides.

Moreover, the risk of immune response following intravenous injection of VEPEP-4 is negligible.

Several aspects of the present invention are further developed in the following examples, illustrated by the figures (which are described in the examples).

Example 1: Materials and Methods

VEPEP-4 Peptides

All peptides were synthesized by solid-phase peptide synthesis using AEDI-expensin resin with (fluorenyl-methoxy)-carbonyl (Fmoc) on a Pioneer Peptide Synthesizer (Pioneer™, Applied Biosystems, Foster City, Calif.) starting from Fmoc-PAL-PEG-PS resin at a 0.2 mmol scale. The coupling reactions were performed with 0.5 M of HATU in the presence of 1 M of DIEA. Protecting group removal and final cleavage from the resin were carried out with TFA/Phenol/$H_2O$/Thioanisol/Ethanedithiol (82.5/5/5/5/2.5%) for 3 h 30 min. All the peptides presented a cysteamide group at the C-terminus and were acetylated at the N-terminus. The peptide synthesis started by the C-terminus, using an AEDI-expensin resin starting with a cysteamide link, as described by Mery et al, 1992 [9]. All the peptides contained a beta-Alanine or a serine at the N-terminus to favour any further functionalization without using the C-terminal cysteamide group.

Functionalization of Vepep-4

Two approaches were used for peptide functionalization (1) Peptide conjugations with peptide, antibody, pegylation, NTA, cholesterol, stearylation, were performed at the primary amino group of the N-terminal residue, through a beta alanine or serine. It is advantageous to maintain the C-terminal cysteamide free, since it is known to be required to stabilize the particle through disulfide bounds (SH—SH). Functionalized peptides were further purified by Reverse Phase-HPLC and analyzed by electro-spray ionization mass spectroscopy.

(2) Peptide conjugations were also performed via disulfide bound using the SH-group of the cysteamide moiety of the peptide.

X: Cholesterol, Pegylation, stearyl, palmitoyl, small FC or FAB fragments, nanobody, nitrilotriacetic acid (2×NTA), tissues targeting peptides (brain, lung, lymphe node, pancreas . . . ).

VEPEP-4 Structure

VEPEP-4 peptides are amphipatic peptides; they are highly versatile and show a strong structural polymorphism. VEPEP-4 are unfolded in solution in free form as well as in the presence of lipid or artificial cellular membranes or of cargos such as peptide or small molecules.

Peptides

Peptides targeting CDK/Cyclin (C4 sequences) or HIV integrase (PC4) cyclic version were used as polypeptide cargoes.

```
C4:
                                              (SEQ ID No: 6)
KKQVRMAHLVLT

C4C:
                                              (SEQ ID No: 7)
CKKQVRMAHLVLTC
```

```
                    -continued
PC4, also noted PC4D
                                              (SEQ ID No: 8)
RWTEWEWW PC4S:
                                              (SEQ ID No: 9)
TWFTEWFT PC6, also noted PC6D:
                                              (SEQ ID No: 10)
KWETWWET PC6S:
                                              (SEQ ID No: 11)
KAETWAET
```

PNA

Short oligonucleotides PNA and 5' $Alexa^{700}$ or Cy5 fluorescently labelled PNA were synthesized by Eurogentec (Belgium) according to the following sequences.

```
Cyc-Bct;
                                              (SEQ ID No: 12)
TGC CAT CAA GCT TAG AG-$^{Cy5}$
```

Fluorescence Titrations

Fluorescence experiments were performed on a PTI spectrofluorimeter at 25° C. in a NaCl 154 mM buffer. Intrinsic Trp-fluorescence of VEPEP-4 was excited at 290 nm and emission spectrum was recorded between 310 and 400 nm, with a spectral band-pass of 2 and 8 nm for excitation and emission, respectively. FITC-fluorescence of labelled-peptide was excited at 492 nm and emission recorded between 500 and 580 nm. For VEPEP-4/peptide interaction, 0.5 µM of FITC-labelled peptide was titrated by increasing concentrations of VEPEP-4. All measurements were corrected for the dilution and curve fitting were performed by using Grafit software (Erithacus).

Characterization of Peptide-Based Nanoparticles

Mean particle size distribution was determined with a Coulter N4 Plus (Coulter-Beckman) at 25° C. for 3 min per measurement and zeta potential was measured with Zetasizer 4 apparatus (Malvern Ltd)

Cell Culture and VEPEP-Mediated Cargo Delivery

Adherent HS68 fibroblasts, HeLa, PC3, CEM-SS, U2OS, MCF-7, and HEK2 cell lines (from American Type Culture Collection (ATCC)), as well as MEF and PBMC, were cultured in Dulbecco's Modified Eagle's Medium supplemented with 2 mM glutamine, 1% antibiotics (streptomycin 10'000 µg/ml, penicillin, 10,000 IU/ml) and 10% (w/v) foetal calf serum (FCS), at 37° C. in a humidified atmosphere containing 5% $CO_2$. Stock solutions of VEPEP-4/peptide particles were prepared by complexing 1 µM peptide with VEPEP-4 peptides at a molar ratio of 1/20 for 30 min at 37° C. Lower concentrations of VEPEP-4-carrier/peptide (from 500 nM to 1 µM) were obtained by serial dilution of the stock complexes in PBS, in order to preserve the same VEPEP-4-carrier/peptide ratio. 150,000 cells seeded in a 35 mm dish the day prior transfection, were grown to 60% confluence and overlaid with 200 µl of preformed complexes, incubated for 3-5 min, then 400 µl of DMEM were added. After 30 min. incubation at 37° C., 1 ml of fresh DMEM containing 16% foetal calf serum (FCS) was added in order to reach a final FCS concentration of 10%, without removing the overlay of VEPEP-4/peptide complexes. Cells were returned to the incubator for 24 hrs. For CDK2 derived peptides cell proliferation was monitored after 24 and 48 hrs. For peptide-targeting integrase, HIV proliferation was analyzed on activated PBMC cells after 3 and 5 days. Data reported are an average of 3 or 4 distinct experiments.

Cytotoxicity

Toxicity of VEPEP-4/peptide or VEPEP-4/SHM complexes was investigated on Hela and HS-68 cell lines. 30,000 cells seeded in 24-well plated the day prior transfection, were incubated with increasing concentrations of peptide or SHM complexed with VEPEP-4 at a 20/1 molar ratio ranging from 1 to 5 µM, for 30 min prior to addition of medium to reach a final 10% concentration of FCS. Cytotoxic response was measured 12 hr or 24 hr later by monitoring the housekeeping gene cyclophilin mRNA level (Quantigen, Panomic Inc.) and by colorimetric MTT assay (Sigma, Germany), respectively. For MTT assay, cell culture medium was removed and replaced with PBS containing 2.5 mg/ml of MTT for 4 hr. Results correspond to the average of 3 separate experiments.

Example 2: VEPEP-4 Peptides Applications for Molecules Delivery

Example 2.1: VEPEP-4 Peptides Form Stable Nanostructures with Peptides

VEPEP-4i (SEQ ID No: 1) and VEPEP-4j (SEQ ID No: 2) peptides form stable complexes with peptides. The binding of cargos to VEPEP-4 was monitored by fluorescence spectroscopy using the both intrinsic Trp group of VEPEP-4 (4 Trp-residues) and extrinsic fluorescently labeled cargoes (using Cy5 or FITC). Curve fitting reveal that VEPEP-4 strongly binds the different cargoes with dissociation constant in the nanomolar range (Table 1 and FIGS. 1A-1D).

TABLE 1

VEPEP-4/Cargo complexes characterization.
Peptide (C4), Cyclic peptide (PC4).
VEPEP-4

| | Cargoes | | | |
|---|---|---|---|---|
| | Peptide | | Cyclic peptide | |
| | Binding | Kd (nM) | Binding | Kd (nM) |
| VEPEP-3i (SEQ ID No: 1) | yes | 10-20 | yes | 50-100 |
| VEPEP-3j (SEQ ID No: 2) | yes | 10-20 | yes | 50-100 |
| Short 3 (SEQ ID No: 3) | yes | 10-20 | yes | 50-100 |
| Short 4 (SEQ ID No: 4) | yes | 10-20 | yes | 50-100 |

Example 2.2: VEPEP-4 Peptides Form Stable Nanostructures with Small Hydrophobic Molecules VEPEP-4 peptides also form stable particles with small aromatic molecules including daunomycin, Paclitaxel, doxorubicin, porphyrin and charged molecules including nucleotide, nucleoside and peptide-analogue of nucleic acids or fluorescent dyes. The dissociation constant for small hydrophobic molecule ranges between 0.05 to 2 µM, depending on the nature of the dyes and of the peptides.

Binding of small molecule cargoes has been investigated in detail depending on the nature of the SMH. Several hydrophobic and charges molecules have been use (Daunomycin, Paclitaxel, doxorubicin, porphyrin) and charged molecules (nucleotide, nucleoside and fluorescent dyes).

TABLE 2

VEPEP-4/Cargo complexes characterization. SHM: small hydrophobic molecules (porphyrin, FAM-G, doxorubicin)
VEPEP-4

| | Cargoes | | | | | |
|---|---|---|---|---|---|---|
| | Doxorubicin | | porphyrin | | FAM-guanosine | |
| | Binding | Kd (µM) | Binding | Kd (µM) | Binding | Kd (µM) |
| VEPEP-3i: | yes | 0.05 | yes | 0.4 | yes | 0.06 |
| VEPEP-3j | yes | 0.07 | yes | 0.5 | yes | 0.05 |
| Short 3 | yes | 0.1 | yes | 0.7 | yes | 0.1 |
| Short 4 | yes | 0.01 | yes | 0.6 | yes | 0.07 |

Figure 2:
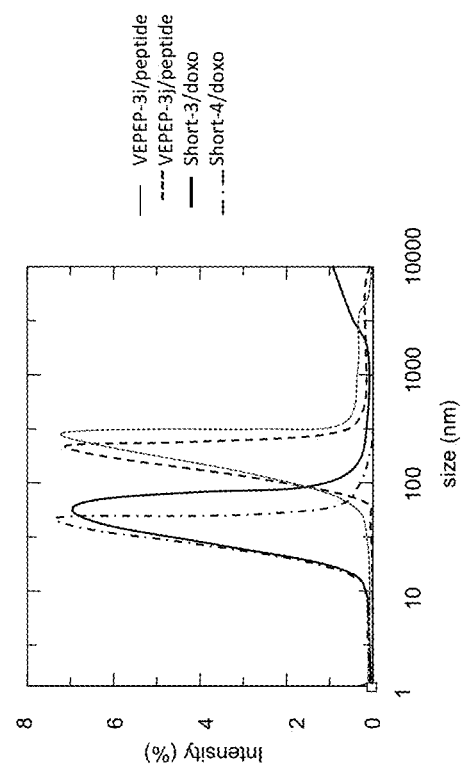
FIG. 2 shows the particle size distribution of VEPEP-4/cargo complexes (VEPEP-3i/peptide, VEPEP-3j/peptide, short 3/Doxo, and short 4/Doxo) at molar ratios ranging between 1:10 and 1:30 (as determined by dynamic light scattering).

Example 2.3: VEPEP-4 Peptides Form Stable Nanoparticles with their Different Cargoes The size of the particles was monitored by dynamic light scattering. The optimal VEPEP-4 peptide/cargo (peptide and SHM) molar ratio is ranging between 1/10 to 1/30 (FIG. 2). The size of the particles is of about 100 to 200 nanometer in diameter.

Example 3: VEPEP-4 Mediated Delivery of Peptide and Cyclic Peptide in Different Cell Lines VEPEP-4 peptides have been used for the delivery of different peptides into different cell lines, including primary cell lines, stem cell lines and challenging cell lines. Peptide delivery was monitored using three approaches, fluorescence spectroscopy and monitoring biological responses (anti proliferation and anti viral responses).

1—Fluorescently labelled peptide was visualized in the different cell lines using fluorescence microscopy or FACS sorting (Table 3). In most of the cell lines, the uptake of Cy-5 labelled peptides is more than 70% of the cells.

Figure 3:
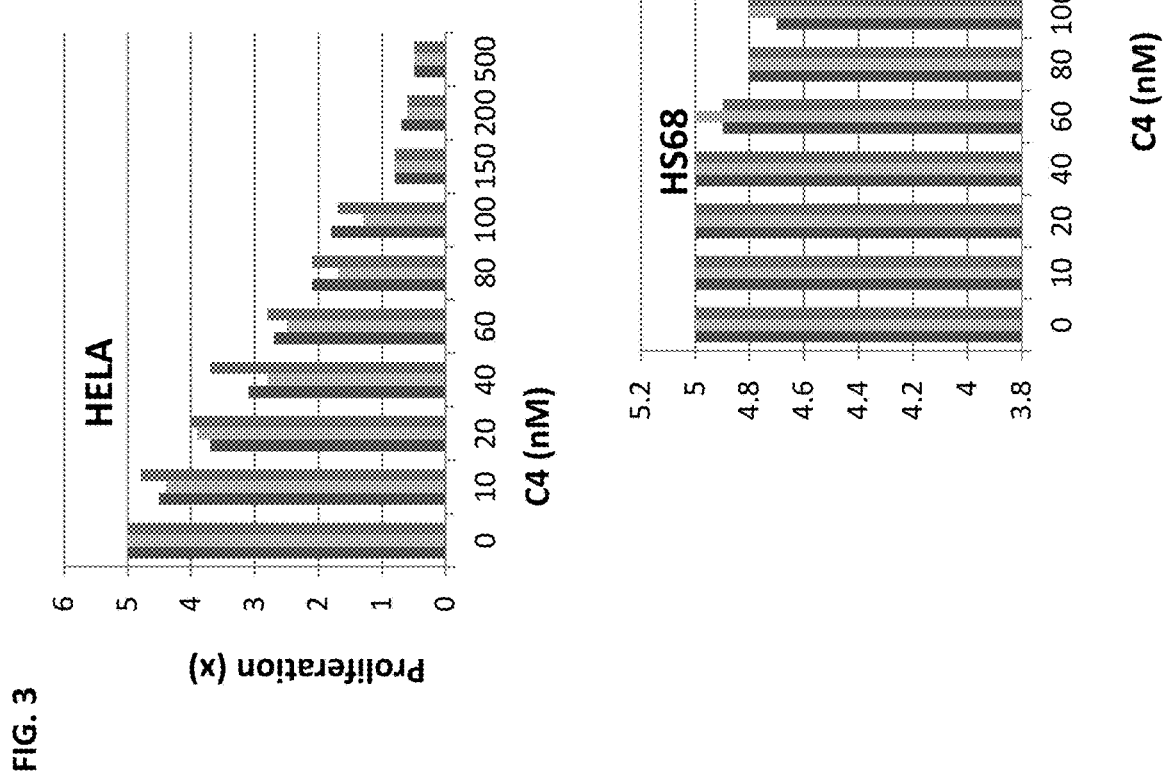
FIG. 3 shows the dose-response of VEPEP-4-mediated delivery of C4 peptides on proliferation in Hela, MCF7 and HS-68. VEPEP-3i, VEPEP-3j, and short 3 peptides were used for C4 delivery.

2—Dose-response experiments performed on different cultured cells revealed that VEPEP-4-mediated delivery of C4 peptides, targeting cdk2/cyclin A complex blocks cell proliferation of different cancer cells (FIG. 3).

Figure 4:
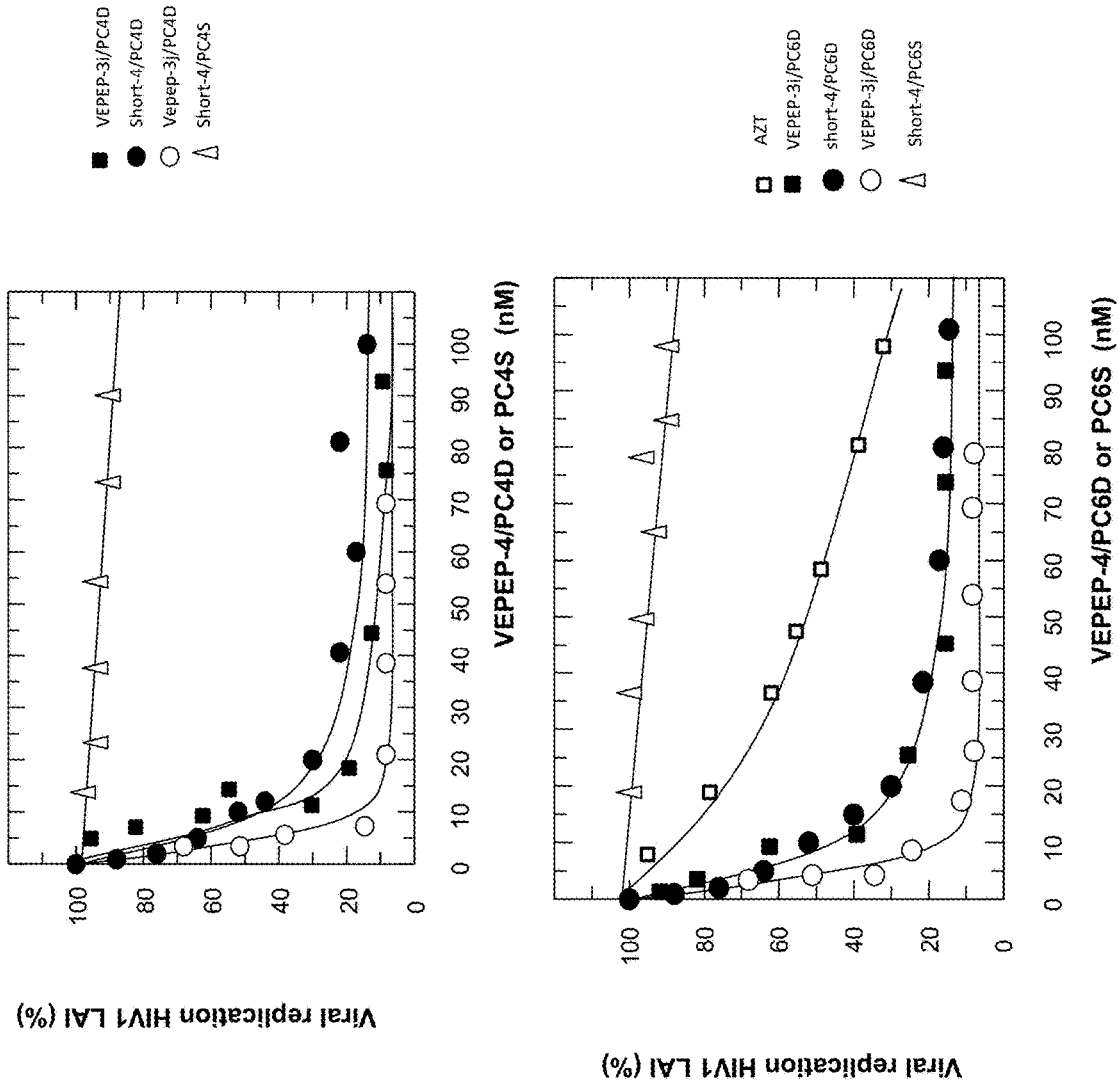
FIG. 4 shows the dose-response of VEPEP-4-mediated delivery of PC4D, PC4S, PC6D, or PC6S peptides on viral replication in HIV-infected PBMCs. VEPEP-3i, VEPEP-3j, and short 4 peptides and AZT were used for PC4D, PC6D, PC4S, or PC6S delivery.

3—Dose-response experiments performed on HIV infected activated PBMC cells revealed that VEPEP-4-mediated delivery of PC4D peptides, targeting pre integration complex and HIV integrase block viral replication (FIG. 4).

TABLE 4

| Cell lines | origin | VEPEP-3i Efficiency | VEPEP-3j Efficiency | Short 4 Efficiency |
|---|---|---|---|---|
| Hela | Human epithelial cervical cells | 65% | 62% | 58% |
| MEF | Mouse fibroblast | 84% | 70% | 67% |
| HS-68 | Human fibroblast | 80% | 80% | 87% |
| CEM-SS | Human macrophage | 70% | 65% | 74% |
| U2OS | Human osteoblast | 78% | 81% | 65% |
| MCF7 | Human breast adenocarcinoma | 50% | 65% | 78% |
| PBMC | Human macrophage | 80% | 80% | 65% |

VEPEP4-Mediated Delivery of Peptide Targeting Cdk2/Cyclin A Block Cancer Cell Proliferation Dose-response experiments performed on cultured cells revealed that VEPEP-4 mediated delivery of C4 peptide induced a robust biological response associated with specific cell cycle arrest (FIG. 3). A peptide C4 concentration of 100 nM was sufficient to block proliferation of Hela and MCF7 cells. $IC_{50}$ of 50±15 nM and 60±12 nM were estimated for C4 peptides respectively on Hela and MCF7. In contrast, proliferation was only reduced by 10 to 20 for non-transformed HS68 fibroblasts (FIG. 3) in perfect agreement with the impact of the check point G2-M on the cell cycle proliferation and showing the specificity of the peptide for cancer cells.

VEPEP4-Mediated Delivery of Peptide Targeting HIV Integrase Block HIV Virus Replication The anti-HIV activities of the peptides (PC4D, PC4S, PC6D, PC6S) and VEPEP-4/peptides complexes were assayed according to previously described method (Roisin et al, 2004). Phytohemagglutinin-P (PHA-P)-activated peripheral blood mononuclear cells (PBMC) treated by increasing concentrations of peptide (from 100 to 0.1 nM), one hour later, were infected with hundred 50% tissue culture infectious doses ($TCID_{50}$) per 100,000 cells of the HIV-1-LAI or different resistant strains (Barre-Sinoussi et al, 1983). Viruses were amplified in vitro on PHA-P-activated PBMC. Viral stock was titrated using PHA-P-activated PBMC, and 50% $TCID_{50}$ were calculated using Karber's formula (Karber 1931). Samples were maintained throughout the culture, and cell supernatants were collected at day 7 post-infection and stored at −20 C. Viral replication was measured by quantifying RT activity in cell culture supernatants. In parallel, cytotoxicity of the compounds was evaluated in uninfected PHA-P-activated PBMC by colorimetric 3-(4-5 dimethylthiazol-2-yl)2,5 diphenyl tetrazolium bromite (MTT) assay on day 7 (Mossmann 1983). Experiments were performed in triplicate and repeated with another blood donor. Data analyses were performed using SoftMax® Pro 4.6 microcomputer software: percent of inhibition of RT activity or of cell viability were plotted vs concentration and fitted with quadratic curves; 50% effective doses ($ED_{50}$) and cytotoxic doses ($CD_{50}$) were calculated.

Dose-response experiments performed on cultured cells revealed that VEPEP-4 mediated delivery of PC4D significantly block viral replication on PBMC infected by HIV-$1_{LAI}$. (FIG. 4). $IC_{50}$ of 0.24±0.1 nM, 0.17±0.07 nM, and 0.37±0.1 nM was obtained for VEPEP-3i, VEPEP-3j, and Short 4, respectively. In contrast, PC4S, the scrambled peptides do not show any anti viral activity. Both VEPEP-4/peptide complexes do not induce a toxic response and a selectivity index greater than 2100.

Example 4: VEPEP4-Mediated Delivery of Peptide and SHM is not Toxic

Figure 5:
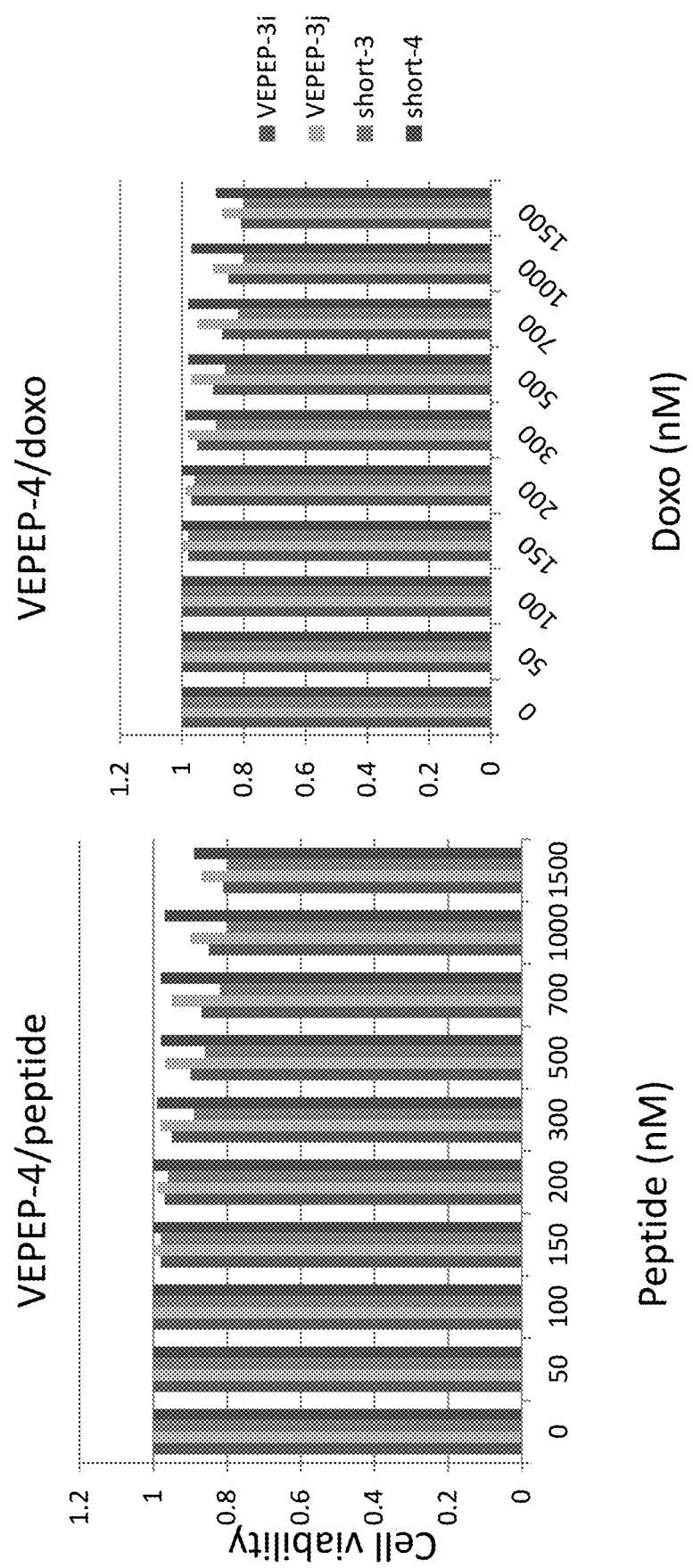
FIG. 5 shows the toxicity profile of VEPEP-4 particles on Hela and U2OS cells (as determined by MTT assay and by cyclophilin mRNA level). VEPEP-3i, VEPEP-3j, short 3 and short 4 peptides were complexed with either peptide or doxorubicin.

As shown on FIG. 5, the toxicity of VEPEP-4-particles was investigated on HeLa and U2OS cells by MTT assay. No toxicity was detected at levels up to 200 nM, and only a mild toxicity was observed at the maximum concentration of 1 µM.

Figure 6:
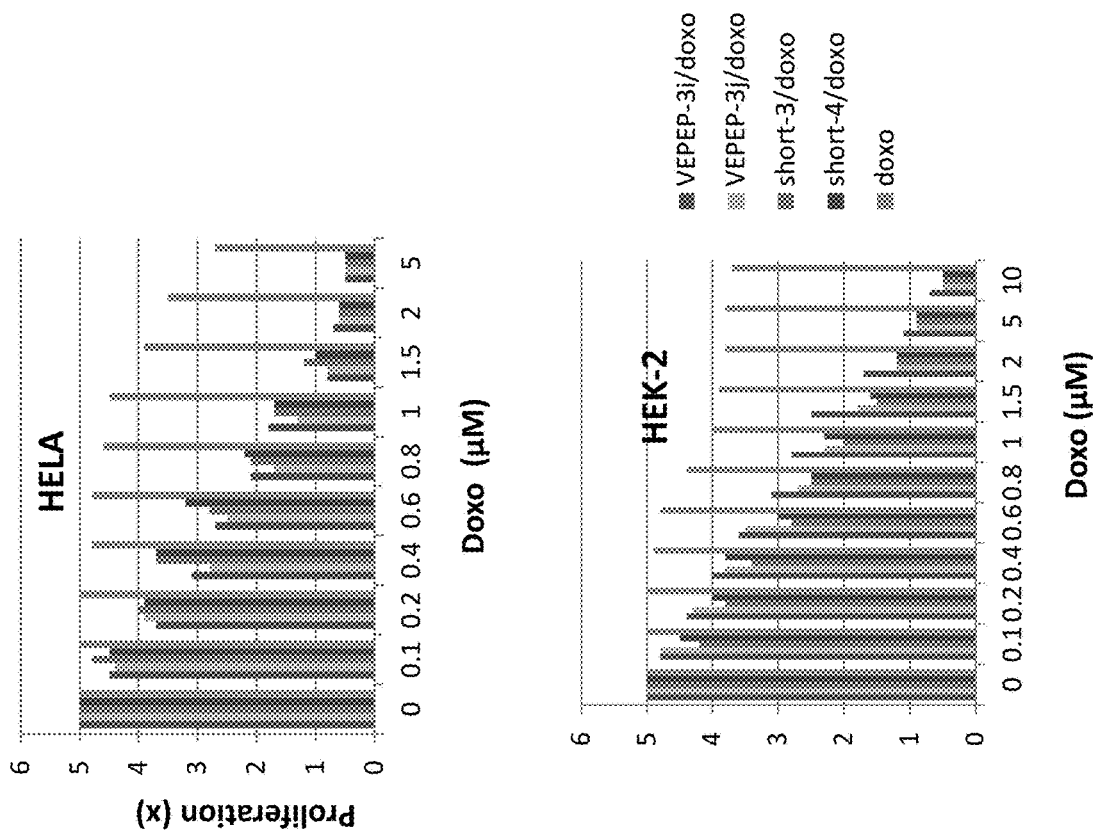
FIG. 6 shows the dose-response of VEPEP-4-mediated delivery of doxorubicin on cancer cell proliferation. VEPEP-3i, VEPEP-3j, short 3 and short 4 peptides were used for delivery in HELA cells or HEK-2 cells.

Example 5: VEPEP-4 Mediated Delivery of Small Hydrophobic Molecule in Different Cell Lines VEPEP-4 peptides have been used for the delivery of different small fluorescent hydrophobic and charged molecules as well as doxorubicin on different cell lines including primary cell lines and challenging cell lines. VEPEP-4 peptides form stable particles with small aromatic molecules including doxorubicin. Effect of VEPEP-4 mediated delivery of doxorubicin has been investigated on cancer cell viability. Dose-response experiments performed on cultured cells revealed that VEPEP-4 mediated delivery of doxorubicin induced a biological response associated to cell cycle arrest and decrease in viability of MCF7, HEK2, Hela cancer cells (FIG. 6). The impact of carrier peptides to improve cellular uptake of small molecule drugs was estimated by following inhibition of proliferation of cancer cells.

Data demonstrated that Doxo is 25 fold more efficient when complexed with VEPEP-4 (Table 5).

TABLE 5

| Drug | VEPEP-3i IC50 (µM) | VEPEP-3j IC50 (µM) | Free drug IC50 (µM) | Short 3 IC50 (µM) | Short 4 IC50 (µM) |
|---|---|---|---|---|---|
| Doxo (HEK2) | 0.4 | 0.3 | 10 | 1.1 | 0.5 |
| Doxo (MCF7) | 0.5 | 0.2 | 7 | 0.9 | 0.5 |
| Doxo (Hela) | 1.2 | 0.8 | 25 | 1.2 | 0.6 |

REFERENCES

[1] D J. Glover, H J. Lipps, D A. Jans, Towards safe, non-viral therapeutic gene expression in humans. Nat. Rev. Genet. 6 (2005) 299-310

[2] K A. Whitehead, R. Langer, D G. Anderson, Knocking down barriers: advances in siRNA delivery. Nat Rev Drug Discov. 8 (2009) 129-138.

[3] Ü Langel, Handbook of Cell-Penetrating Peptides: (Eds.: U. Langel) CRC Taylor & Francis, Boca Raton (2007).

[4] F. Heitz, M C. Morris, G. Divita, Twenty years of cell-penetrating peptides: from molecular mechanisms to therapeutics; British Journal of Pharmacology 157 (2009) 195-206.

[5] S. Deshayes, M C Morris, F. Heitz, G. Divita. Delivery of proteins and nucleic acids using a non-covalent peptide-based strategy. Adv Drug Deliv Rev. 60 (2008) 537-547.

[6] S. Deshayes, M C. Morris, G. Divita, F. Heitz Cell-penetrating peptides: tools for intracellular delivery of therapeutics, Cell Mol Life Sci. 62 (2005) 1839-1849.

[7] M C. Morris, P. Vidal, L. Chaloin, F. Heitz, G Divita A new peptide vector for efficient delivery of oligonucleotides into mammalian cells, Nucleic Acids Res. 25 (1997) 2730-2736.

[8] M C. Morris, J. Depollier, J. Mery, F. Heitz, G. Divita A peptide carrier for the delivery of biologically active proteins into mammalian cells, Nat. Biotechnol. 19 (2001) 1173-1176.

[9] Mery J, Brugidou J, Derancourt J. Disulfide bond as peptide-resin linkage in Boc-Bzl SPPS, for potential biochemical applications, Pept Res. 1992 July-August; 5(4):233-40.

[10] L. Crombez, M. C. Morris, S. Dufort, G. Aldrian-Herrada, Q. Nguyen, G. Mc Master, J. L. Coll, F. Heitz, G. Divita, Targeting cyclin B1 through peptide-based delivery of siRNA prevents tumour growth, Nucleic Acids Res. 37 (2009) 4559-4569.

[11] L. Crombez, G. Aldrian-Herrada, K. Konate, Q. N. Nguyen, G. K. McMaster, R. Brasseur, F. Heitz, G. Divita, A new potent secondary amphipathic cell-penetrating peptide for siRNA delivery into mammalian cells, Mol. Ther. 17 (2009) 95-103.

[12] Verdine, G. L. and Hilinski, G. J. (2012), Stapled peptides for intracellular drug targets. Methods in Enzymology, vol 503, p 3-33.

The invention claimed is:

1. A cell-penetrating peptide characterized in that it comprises an amino acid sequence consisting of $X_1WX_2RLX_3X_4X_5X_6X_7X_8$ (SEQ ID No: 5), wherein $X_1$ is beta-A or S; $X_2$, $X_6$, and $X_7$ are, independently from each other, W or F; $X_5$ is S or R, and $X_8$ is R or none, and wherein $X_3$ is R if $X_5$ is S, $X_3$ is S if $X_5$ is R, $X_4$ is L or none if $X_8$ is R, and $X_4$ is L if $X_8$ is none.

2. The cell-penetrating peptide of claim 1, wherein the amino acid sequence is selected from the group consisting of:

$X_1$WWRLSLRWW, (SEQ ID No:. 1)

$X_1$WFRLSLRFWR, (SEQ ID No: 2)

$X_1$WWRLRSWFR, (SEQ ID No: 3)
and $X_1$WFRLSLRFW, (SEQ ID No: 4)

wherein $X_1$ is beta-A or S.

3. The cell-penetrating peptide of claim 1, further comprising, covalently linked to the N-terminal end of the amino acid sequence, one or several chemical entities selected in the group consisting of an acetyl, a fatty acid, a cholesterol, a poly-ethylene glycol, a nuclear localization signal, a nuclear export signal, an antibody, a polysaccharide and a targeting molecule.

4. The cell-penetrating peptide of claim 1, further comprising, covalently linked to the C-terminal end of said amino acid sequence, one or several groups selected in the group consisting of a cysteamide, a cysteine, a thiol, an amide, a nitrilotriacetic acid optionally substituted, a carboxyl, a linear or ramified $C_1$-$C_6$ alkyl optionally substituted, a primary or secondary amine, an osidic derivative, a lipid, a phospholipid, a fatty acid, a cholesterol, a polyethylene glycol, a nuclear localization signal, a nuclear export signal, an antibody, a polysaccharide and a targeting molecule.

5. A complex comprising a cell-penetrating peptide according to claim 1 and a cargo selected from the group consisting of peptides, uncharged oligonucleotides, peptide nucleic acids (PNAs) and small hydrophobic molecules.

6. The complex of claim 5, wherein said cargo is a molecule of at most 1.5 kDa.

7. The complex of claim 5, wherein said cargo is an anticancer drug or an antiviral drug.

8. The complex of claim 5, wherein said cargo is selected from the group consisting of amino acids, di-peptides, tri-peptides, daunomycin, paclitaxel, doxorubicin, azidothymidine (AZT), porphyrin, fluorescently labelled nucleosides and nucleotides, hydrophobic maghemite and fluorescent dyes.

9. The complex of claim 5, wherein said cargo is a cosmetic agent.

10. The complex of claim 5, wherein the size of the complex is between 50 nm and 200 nm.

11. A nanoparticle comprising a complex according to claim 5, coated by a layer of peripheral cell-penetrating peptides, wherein said cell-penetrating peptides have a peptide sequence different from SEQ ID No: 5.

12. A nanoparticle comprising a core which comprises a cargo complexed to a first entity selected from the group consisting of cell-penetrating peptides, liposomes, polycationic structures and carbon nanoparticles, wherein said core is coated by a cell-penetrating peptide according to claim 1.

13. The nanoparticle of claim 12, wherein said first entity is a cell penetrating peptide selected from the group consisting of VEPEP-3, VEPEP-6, VEPEP-9, CADY, MPG, PEP-1, PPTG 1, and poly Arginine motif.

14. The nanoparticle of claim 12, wherein the size of the nanoparticle is between 20 nm and 300 nm.

15. A therapeutic, cosmetic or diagnostic composition comprising a nanoparticle according to claim 12.

16. A method for delivering a molecule into a cell in vitro, comprising a step of contacting said cell with a nanoparticle according to claim 12, which comprises said molecule.

* * * * *

SEQUENCE LISTING

<160> NUMBER OF SEQ ID NOS: 46

<210> SEQ ID NO 1
<211> LENGTH: 10
<212> TYPE: PRT
<213> ORGANISM: Artificial
<220> FEATURE:
<223> OTHER INFORMATION: synthesized peptide Short 1 VEPEP-3i
<220> FEATURE:
<221> NAME/KEY: MISC_FEATURE
<222> LOCATION: (1)..(1)
<223> OTHER INFORMATION: X = beta-A or S

<400> SEQUENCE: 1

Xaa Trp Trp Arg Leu Ser Leu Arg Trp Trp
1               5                   10

<210> SEQ ID NO 2
<211> LENGTH: 11
<212> TYPE: PRT
<213> ORGANISM: Artificial
<220> FEATURE:
<223> OTHER INFORMATION: synthesized peptide Short 2 VEPEP-3j
<220> FEATURE:
<221> NAME/KEY: MISC_FEATURE
<222> LOCATION: (1)..(1)
<223> OTHER INFORMATION: X = beta-A or S

<400> SEQUENCE: 2

Xaa Trp Phe Arg Leu Ser Leu Arg Phe Trp Arg
1               5                   10

<210> SEQ ID NO 3
<211> LENGTH: 10
<212> TYPE: PRT
<213> ORGANISM: Artificial
<220> FEATURE:
<223> OTHER INFORMATION: synthesized peptide Short 3
<220> FEATURE:
<221> NAME/KEY: MISC_FEATURE
<222> LOCATION: (1)..(1)
<223> OTHER INFORMATION: X = beta-A or S

<400> SEQUENCE: 3

Xaa Trp Trp Arg Leu Arg Ser Trp Phe Arg
1               5                   10

<210> SEQ ID NO 4
<211> LENGTH: 10
<212> TYPE: PRT
<213> ORGANISM: Artificial
<220> FEATURE:
<223> OTHER INFORMATION: synthesized peptide Short 4
<220> FEATURE:
<221> NAME/KEY: MISC_FEATURE
<222> LOCATION: (1)..(1)
<223> OTHER INFORMATION: X = beta-A or S

<400> SEQUENCE: 4

Xaa Trp Phe Arg Leu Ser Leu Arg Phe Trp
1               5                   10

<210> SEQ ID NO 5
<211> LENGTH: 11
<212> TYPE: PRT
<213> ORGANISM: Artificial
<220> FEATURE:
<223> OTHER INFORMATION: synthesized peptide Group 1
<220> FEATURE:
<221> NAME/KEY: MISC_FEATURE

```
<222> LOCATION: (1)..(1)
<223> OTHER INFORMATION: X = beta-A or S
<220> FEATURE:
<221> NAME/KEY: MISC_FEATURE
<222> LOCATION: (3)..(3)
<223> OTHER INFORMATION: X = W or F
<220> FEATURE:
<221> NAME/KEY: MISC_FEATURE
<222> LOCATION: (6)..(6)
<223> OTHER INFORMATION: X = R if X in position 8 is S or S if X in
      position 8 is R
<220> FEATURE:
<221> NAME/KEY: MISC_FEATURE
<222> LOCATION: (7)..(7)
<223> OTHER INFORMATION: X = L or none, and X is L if X in position 11
      is none
<220> FEATURE:
<221> NAME/KEY: MISC_FEATURE
<222> LOCATION: (8)..(8)
<223> OTHER INFORMATION: X = S or R
<220> FEATURE:
<221> NAME/KEY: MISC_FEATURE
<222> LOCATION: (9)..(9)
<223> OTHER INFORMATION: X = W or F
<220> FEATURE:
<221> NAME/KEY: MISC_FEATURE
<222> LOCATION: (10)..(10)
<223> OTHER INFORMATION: X = W or F
<220> FEATURE:
<221> NAME/KEY: MISC_FEATURE
<222> LOCATION: (11)..(11)
<223> OTHER INFORMATION: X = R or none

<400> SEQUENCE: 5

Xaa Trp Xaa Arg Leu Xaa Xaa Xaa Xaa Xaa Xaa
1               5                   10

<210> SEQ ID NO 6
<211> LENGTH: 12
<212> TYPE: PRT
<213> ORGANISM: Artificial
<220> FEATURE:
<223> OTHER INFORMATION: synthesized peptide C4

<400> SEQUENCE: 6

Lys Lys Gln Val Arg Met Ala His Leu Val Leu Thr
1               5                   10

<210> SEQ ID NO 7
<211> LENGTH: 14
<212> TYPE: PRT
<213> ORGANISM: Artificial
<220> FEATURE:
<223> OTHER INFORMATION: synthesized peptide C4C

<400> SEQUENCE: 7

Cys Lys Lys Gln Val Arg Met Ala His Leu Val Leu Thr Cys
1               5                   10

<210> SEQ ID NO 8
<211> LENGTH: 8
<212> TYPE: PRT
<213> ORGANISM: Artificial
<220> FEATURE:
<223> OTHER INFORMATION: synthesized peptide PC4

<400> SEQUENCE: 8

Arg Trp Thr Glu Trp Glu Trp Trp
1               5

<210> SEQ ID NO 9
```

```
<211> LENGTH: 8
<212> TYPE: PRT
<213> ORGANISM: Artificial
<220> FEATURE:
<223> OTHER INFORMATION: synthesized peptide PC4S

<400> SEQUENCE: 9

Thr Trp Phe Thr Glu Trp Phe Thr
1               5

<210> SEQ ID NO 10
<211> LENGTH: 8
<212> TYPE: PRT
<213> ORGANISM: Artificial
<220> FEATURE:
<223> OTHER INFORMATION: synthesized peptide PC6

<400> SEQUENCE: 10

Lys Trp Glu Thr Trp Trp Glu Thr
1               5

<210> SEQ ID NO 11
<211> LENGTH: 8
<212> TYPE: PRT
<213> ORGANISM: Artificial
<220> FEATURE:
<223> OTHER INFORMATION: synthesized peptide PC6S

<400> SEQUENCE: 11

Lys Ala Glu Thr Trp Ala Glu Thr
1               5

<210> SEQ ID NO 12
<211> LENGTH: 18
<212> TYPE: DNA
<213> ORGANISM: Artificial
<220> FEATURE:
<223> OTHER INFORMATION: synthesized oligonucleotide Cyc-Bct

<400> SEQUENCE: 12
tgccatcaag cttagagg                                                    18

<210> SEQ ID NO 13
<211> LENGTH: 16
<212> TYPE: PRT
<213> ORGANISM: Artificial
<220> FEATURE:
<223> OTHER INFORMATION: synthesized peptide VEPEP-3a
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (16)..(16)
<223> OTHER INFORMATION: residue covalently linked to cysteamide

<400> SEQUENCE: 13

Xaa Lys Trp Phe Glu Arg Trp Phe Arg Glu Trp Pro Arg Lys Arg Arg
1               5                   10                  15

<210> SEQ ID NO 14
<211> LENGTH: 16
<212> TYPE: PRT
<213> ORGANISM: Artificial
```

<220> FEATURE:
<223> OTHER INFORMATION: synthesized peptide VEPEP-3b
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (16)..(16)
<223> OTHER INFORMATION: residue covalently linked to cysteamide

<400> SEQUENCE: 14

Xaa Lys Trp Trp Glu Arg Trp Trp Arg Glu Trp Pro Arg Lys Arg Lys
1               5                   10                  15

<210> SEQ ID NO 15
<211> LENGTH: 16
<212> TYPE: PRT
<213> ORGANISM: Artificial
<220> FEATURE:
<223> OTHER INFORMATION: synthesized peptide VEPEP-3c
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (16)..(16)
<223> OTHER INFORMATION: residue covalently linked to cysteamide

<400> SEQUENCE: 15

Xaa Arg Trp Trp Glu Lys Trp Trp Thr Arg Trp Pro Arg Lys Arg Lys
1               5                   10                  15

<210> SEQ ID NO 16
<211> LENGTH: 16
<212> TYPE: PRT
<213> ORGANISM: Artificial
<220> FEATURE:
<223> OTHER INFORMATION: synthesized peptide VEPEP-3d
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (16)..(16)
<223> OTHER INFORMATION: residue covalently linked to cysteamide

<400> SEQUENCE: 16

Xaa Arg Trp Tyr Glu Lys Trp Tyr Thr Glu Phe Pro Arg Arg Arg Arg
1               5                   10                  15

<210> SEQ ID NO 17
<211> LENGTH: 17
<212> TYPE: PRT
<213> ORGANISM: Artificial
<220> FEATURE:
<223> OTHER INFORMATION: synthesized peptide VEPEP-3e
<220> FEATURE:
<221> NAME/KEY: MISC_FEATURE

```
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (17)..(17)
<223> OTHER INFORMATION: residue covalently linked to cysteamide

<400> SEQUENCE: 17

Xaa Arg Trp Trp Arg Leu Trp Trp Arg Ser Trp Phe Arg Leu Trp Arg
1               5                   10                  15

Arg

<210> SEQ ID NO 18
<211> LENGTH: 17
<212> TYPE: PRT
<213> ORGANISM: Artificial
<220> FEATURE:
<223> OTHER INFORMATION: synthesized peptide VEPEP-3f
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (17)..(17)
<223> OTHER INFORMATION: residue covalently linked to cysteamide

<400> SEQUENCE: 18

Xaa Leu Trp Trp Arg Arg Trp Trp Ser Arg Trp Trp Pro Arg Trp Arg
1               5                   10                  15

Arg

<210> SEQ ID NO 19
<211> LENGTH: 17
<212> TYPE: PRT
<213> ORGANISM: Artificial
<220> FEATURE:
<223> OTHER INFORMATION: synthesized peptide VEPEP-3g
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (17)..(17)
<223> OTHER INFORMATION: residue covalently linked to cysteamide

<400> SEQUENCE: 19

Xaa Leu Trp Trp Ser Arg Trp Trp Arg Ser Trp Phe Arg Leu Trp Phe
1               5                   10                  15

Arg

<210> SEQ ID NO 20
<211> LENGTH: 17
<212> TYPE: PRT
<213> ORGANISM: Artificial
<220> FEATURE:
<223> OTHER INFORMATION: synthesized peptide VEPEP-3h
```

```
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (17)..(17)
<223> OTHER INFORMATION: residue covalently linked to cysteamide

<400> SEQUENCE: 20

Xaa Lys Phe Trp Ser Arg Phe Trp Arg Ser Trp Phe Arg Leu Trp Arg
1               5                   10                  15

Arg

<210> SEQ ID NO 21
<211> LENGTH: 19
<212> TYPE: PRT
<213> ORGANISM: Artificial
<220> FEATURE:
<223> OTHER INFORMATION: synthesized peptide VEPEP-6a
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (19)..(19)
<223> OTHER INFORMATION: residue covalently linked to cysteamide

<400> SEQUENCE: 21

Xaa Leu Phe Arg Ala Leu Trp Arg Leu Leu Arg Ser Leu Trp Arg Leu
1               5                   10                  15

Leu Trp Lys

<210> SEQ ID NO 22
<211> LENGTH: 20
<212> TYPE: PRT
<213> ORGANISM: Artificial
<220> FEATURE:
<223> OTHER INFORMATION: synthesized peptide VEPEP-6b
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (20)..(20)
<223> OTHER INFORMATION: residue covalently linked to cysteamide

<400> SEQUENCE: 22

Xaa Leu Trp Arg Ala Leu Trp Arg Leu Trp Arg Ser Leu Trp Arg Leu
1               5                   10                  15

Leu Trp Lys Ala
            20

<210> SEQ ID NO 23
<211> LENGTH: 20
<212> TYPE: PRT
```

-continued

```
<213> ORGANISM: Artificial
<220> FEATURE:
<223> OTHER INFORMATION: synthesized peptide VEPEP-6c
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (20)..(20)
<223> OTHER INFORMATION: residue covalently linked to cysteamide

<400> SEQUENCE: 23

Xaa Leu Trp Arg Ala Leu Trp Arg Leu Leu Arg Ser Leu Trp Arg Leu
1               5                   10                  15

Trp Arg Lys Ala
            20

<210> SEQ ID NO 24
<211> LENGTH: 20
<212> TYPE: PRT
<213> ORGANISM: Artificial
<220> FEATURE:
<223> OTHER INFORMATION: synthesized peptide VEPEP-6d
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (20)..(20)
<223> OTHER INFORMATION: residue covalently linked to cysteamide

<400> SEQUENCE: 24

Xaa Leu Trp Arg Ala Leu Trp Arg Leu Trp Arg Ser Leu Trp Arg Leu
1               5                   10                  15

Trp Arg Lys Ala
            20

<210> SEQ ID NO 25
<211> LENGTH: 20
<212> TYPE: PRT
<213> ORGANISM: Artificial
<220> FEATURE:
<223> OTHER INFORMATION: synthesized peptide VEPEP-6e
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (20)..(20)
<223> OTHER INFORMATION: residue covalently linked to cysteamide

<400> SEQUENCE: 25

Xaa Leu Trp Arg Ala Leu Trp Arg Leu Leu Arg Ala Leu Trp Arg Leu
1               5                   10                  15

Leu Trp Lys Ala
            20
```

```
<210> SEQ ID NO 26
<211> LENGTH: 20
<212> TYPE: PRT
<213> ORGANISM: Artificial
<220> FEATURE:
<223> OTHER INFORMATION: synthesized peptide VEPEP-6f
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (20)..(20)
<223> OTHER INFORMATION: residue covalently linked to cysteamide

<400> SEQUENCE: 26

Xaa Leu Trp Arg Ala Leu Trp Arg Leu Leu Arg Asn Leu Trp Arg Leu
 1               5                  10                  15

Leu Trp Lys Ala
            20

<210> SEQ ID NO 27
<211> LENGTH: 20
<212> TYPE: PRT
<213> ORGANISM: Artificial
<220> FEATURE:
<223> OTHER INFORMATION: synthesized peptide VEPEP-9a1
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (20)..(20)
<223> OTHER INFORMATION: residue covalently linked to cysteamide

<400> SEQUENCE: 27

Xaa Leu Arg Trp Trp Leu Arg Trp Ala Ser Arg Trp Phe Ser Arg Trp
 1               5                  10                  15

Ala Trp Trp Arg
            20

<210> SEQ ID NO 28
<211> LENGTH: 20
<212> TYPE: PRT
<213> ORGANISM: Artificial
<220> FEATURE:
<223> OTHER INFORMATION: synthesized peptide VEPEP-9a2
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (20)..(20)
<223> OTHER INFORMATION: residue covalently linked to cysteamide

<400> SEQUENCE: 28
```

-continued

Xaa Leu Arg Trp Trp Leu Arg Trp Ala Ser Arg Trp Ala Ser Arg Trp
1               5                   10                  15

Ala Trp Phe Arg
            20

<210> SEQ ID NO 29
<211> LENGTH: 19
<212> TYPE: PRT
<213> ORGANISM: Artificial
<220> FEATURE:
<223> OTHER INFORMATION: synthesized peptide VEPEP-9b1
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (19)..(19)
<223> OTHER INFORMATION: acetylated residue cysteamide

<400> SEQUENCE: 29

Xaa Arg Trp Trp Leu Arg Trp Ala Ser Arg Trp Ala Leu Ser Trp Arg
1               5                   10                  15

Trp Trp Arg

<210> SEQ ID NO 30
<211> LENGTH: 19
<212> TYPE: PRT
<213> ORGANISM: Artificial
<220> FEATURE:
<223> OTHER INFORMATION: synthesized peptide VEPEP-9b2
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (19)..(19)
<223> OTHER INFORMATION: residue covalently linked to cysteamide

<400> SEQUENCE: 30

Xaa Arg Trp Trp Leu Arg Trp Ala Ser Arg Trp Phe Leu Ser Trp Arg
1               5                   10                  15

Trp Trp Arg

<210> SEQ ID NO 31
<211> LENGTH: 19
<212> TYPE: PRT
<213> ORGANISM: Artificial
<220> FEATURE:
<223> OTHER INFORMATION: synthesized peptide VEPEP-9c1
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (19)..(19)
<223> OTHER INFORMATION: residue covalently linked to cysteamide

<400> SEQUENCE: 31

Xaa Arg Trp Trp Leu Arg Trp Ala Pro Arg Trp Phe Pro Ser Trp Arg
1               5                   10                  15

Trp Trp Arg

<210> SEQ ID NO 32
<211> LENGTH: 19
<212> TYPE: PRT
<213> ORGANISM: Artificial
<220> FEATURE:
<223> OTHER INFORMATION: synthesized peptide VEPEP-9c2
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (19)..(19)
<223> OTHER INFORMATION: residue covalently linked to cysteamide

<400> SEQUENCE: 32

Xaa Arg Trp Trp Leu Arg Trp Ala Ser Arg Trp Ala Pro Ser Trp Arg
1               5                   10                  15

Trp Trp Arg

<210> SEQ ID NO 33
<211> LENGTH: 15
<212> TYPE: PRT
<213> ORGANISM: Artificial
<220> FEATURE:
<223> OTHER INFORMATION: synthesized peptide VEPEP-9d
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (15)..(15)
<223> OTHER INFORMATION: residue covalently linked to cysteamide

<400> SEQUENCE: 33

Xaa Trp Trp Arg Trp Trp Ala Ser Trp Ala Arg Ser Trp Trp Arg
1               5                   10                  15

<210> SEQ ID NO 34
<211> LENGTH: 15
<212> TYPE: PRT
<213> ORGANISM: Artificial
<220> FEATURE:
<223> OTHER INFORMATION: synthesized peptide VEPEP-9e
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (15)..(15)
<223> OTHER INFORMATION: residue covalently linked to cysteamide

<400> SEQUENCE: 34

Xaa Trp Trp Gly Ser Trp Ala Thr Pro Arg Arg Arg Trp Trp Arg
1               5                   10                  15

<210> SEQ ID NO 35
<211> LENGTH: 15
<212> TYPE: PRT
<213> ORGANISM: Artificial
<220> FEATURE:
<223> OTHER INFORMATION: synthesized peptide VEPEP-9f
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (15)..(15)
<223> OTHER INFORMATION: residue covalently linked to cysteamide

<400> SEQUENCE: 35

Xaa Trp Trp Arg Trp Trp Ala Pro Trp Ala Arg Ser Trp Trp Arg
1               5                   10                  15

<210> SEQ ID NO 36
<211> LENGTH: 17
<212> TYPE: PRT
<213> ORGANISM: Artificial
<220> FEATURE:
<223> OTHER INFORMATION: synthesized peptide VEPEP-3bstapl
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (3)..(3)
<223> OTHER INFORMATION: X =  R, which is linked to the R residue at
      position 10 by a hydrocarbon linkage
<220> FEATURE:
<221> NAME/KEY: MISC_FEATURE
<222> LOCATION: (10)..(10)
<223> OTHER INFORMATION: X =  R, which is linked to the R residue at
      position 3 by a hydrocarbon linkage
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: MISC_FEATURE
<222> LOCATION: (17)..(17)
<223> OTHER INFORMATION: residue covalently linked to cysteamide

<400> SEQUENCE: 36

Xaa Lys Xaa Trp Trp Glu Arg Trp Trp Arg Xaa Trp Pro Arg Lys Arg
1               5                   10                  15

Lys

<210> SEQ ID NO 37
<211> LENGTH: 17
<212> TYPE: PRT
<213> ORGANISM: Artificial
<220> FEATURE:
<223> OTHER INFORMATION: synthesized peptide VEPEP-3estapl

```
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (5)..(5)
<223> OTHER INFORMATION: X = R, which is linked to the S residue at
      position 12 by a hydrocarbon linkage
<220> FEATURE:
<221> NAME/KEY: MISC_FEATURE
<222> LOCATION: (12)..(12)
<223> OTHER INFORMATION: X = S, which is linked to the R residue at
      position 5 by a hydrocarbon linkage
<220> FEATURE:
<221> NAME/KEY: MISC_FEATURE
<222> LOCATION: (17)..(17)
<223> OTHER INFORMATION: residue covalently linked to cysteamide

<400> SEQUENCE: 37

Xaa Arg Trp Trp Xaa Leu Trp Trp Arg Ser Trp Xaa Arg Leu Trp Arg
1               5                   10                  15

Arg

<210> SEQ ID NO 38
<211> LENGTH: 19
<212> TYPE: PRT
<213> ORGANISM: Artificial
<220> FEATURE:
<223> OTHER INFORMATION: synthesized peptide ST-VEPEP-6a
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (8)..(8)
<223> OTHER INFORMATION: X = R, which is linked to the S residue at
      position 12 by a hydrocarbon linkage
<220> FEATURE:
<221> NAME/KEY: MISC_FEATURE
<222> LOCATION: (12)..(12)
<223> OTHER INFORMATION: X = S, which is linked to the R residue at
      position 8 by a hydrocarbon linkage
<220> FEATURE:
<221> NAME/KEY: MISC_FEATURE
<222> LOCATION: (19)..(19)
<223> OTHER INFORMATION: residue covalently linked to cysteamide

<400> SEQUENCE: 38

Xaa Leu Phe Arg Ala Leu Trp Xaa Leu Leu Arg Xaa Leu Trp Arg Leu
1               5                   10                  15

Leu Trp Lys

<210> SEQ ID NO 39
<211> LENGTH: 19
<212> TYPE: PRT
<213> ORGANISM: Artificial
<220> FEATURE:
<223> OTHER INFORMATION: synthesized peptide ST-VEPEP-6aa
<220> FEATURE:
<221> NAME/KEY: MISC_FEATURE
<222> LOCATION: (1)..(1)
<223> OTHER INFORMATION: acetylated residue
<220> FEATURE:
```

```
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (8)..(8)
<223> OTHER INFORMATION: X =  R, which is linked to the S residue at
      position 12 by a hydrocarbon linkage
<220> FEATURE:
<221> NAME/KEY: MISC_FEATURE
<222> LOCATION: (12)..(12)
<223> OTHER INFORMATION: X =  S, which is linked to the R residue at
      position 8 by a hydrocarbon linkage
<220> FEATURE:
<221> NAME/KEY: MISC_FEATURE
<222> LOCATION: (19)..(19)
<223> OTHER INFORMATION: residue covalently linked to cysteamide

<400> SEQUENCE: 39

Xaa Leu Phe Leu Ala Arg Trp Xaa Leu Leu Arg Xaa Leu Trp Arg Leu
1               5                   10                  15

Leu Trp Lys

<210> SEQ ID NO 40
<211> LENGTH: 19
<212> TYPE: PRT
<213> ORGANISM: Artificial
<220> FEATURE:
<223> OTHER INFORMATION: synthesized peptide ST-VEPEP-6ab
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (8)..(8)
<223> OTHER INFORMATION: X =  S, which is linked to the S residue at
      position 12 by a hydrocarbon linkage
<220> FEATURE:
<221> NAME/KEY: MISC_FEATURE
<222> LOCATION: (12)..(12)
<223> OTHER INFORMATION: X =  S, which is linked to the S residue at
      position 8 by a hydrocarbon linkage
<220> FEATURE:
<221> NAME/KEY: MISC_FEATURE
<222> LOCATION: (19)..(19)
<223> OTHER INFORMATION: residue covalently linked to cysteamide

<400> SEQUENCE: 40

Xaa Leu Phe Arg Ala Leu Trp Xaa Leu Leu Arg Xaa Leu Trp Arg Leu
1               5                   10                  15

Leu Trp Lys

<210> SEQ ID NO 41
<211> LENGTH: 19
<212> TYPE: PRT
<213> ORGANISM: Artificial
<220> FEATURE:
<223> OTHER INFORMATION: synthesized peptide ST-VEPEP-6ad
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
```

```
<222> LOCATION: (8)..(8)
<223> OTHER INFORMATION: X = S, which is linked to the S residue at
      position 12 by a hydrocarbon linkage
<220> FEATURE:
<221> NAME/KEY: MISC_FEATURE
<222> LOCATION: (12)..(12)
<223> OTHER INFORMATION: X = S, which is linked to the S residue at
      position 8 by a hydrocarbon linkage
<220> FEATURE:
<221> NAME/KEY: MISC_FEATURE
<222> LOCATION: (19)..(19)
<223> OTHER INFORMATION: residue covalently linked to cysteamide

<400> SEQUENCE: 41

Xaa Leu Phe Leu Ala Arg Trp Xaa Leu Leu Arg Xaa Leu Trp Arg Leu
1               5                   10                  15

Leu Trp Lys

<210> SEQ ID NO 42
<211> LENGTH: 19
<212> TYPE: PRT
<213> ORGANISM: Artificial
<220> FEATURE:
<223> OTHER INFORMATION: synthesized peptide ST-VEPEP-6b
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (11)..(11)
<223> OTHER INFORMATION: X = R, which is linked to the S residue at
      position 15 by a hydrocarbon linkage
<220> FEATURE:
<221> NAME/KEY: MISC_FEATURE
<222> LOCATION: (15)..(15)
<223> OTHER INFORMATION: X = S, which is linked to the R residue at
      position 11 by a hydrocarbon linkage
<220> FEATURE:
<221> NAME/KEY: MISC_FEATURE
<222> LOCATION: (19)..(19)
<223> OTHER INFORMATION: residue covalently linked to cysteamide

<400> SEQUENCE: 42

Xaa Leu Phe Arg Ala Leu Trp Arg Leu Leu Xaa Ser Leu Trp Xaa Leu
1               5                   10                  15

Leu Trp Lys

<210> SEQ ID NO 43
<211> LENGTH: 19
<212> TYPE: PRT
<213> ORGANISM: Artificial
<220> FEATURE:
<223> OTHER INFORMATION: synthesized peptide ST-VEPEP-6ba
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (11)..(11)
<223> OTHER INFORMATION: X = R, which is linked to the S residue at
      position 15 by a hydrocarbon linkage
<220> FEATURE:
<221> NAME/KEY: MISC_FEATURE
```

```
<222> LOCATION: (15)..(15)
<223> OTHER INFORMATION: X = S, which is linked to the R residue at
      position 11 by a hydrocarbon linkage
<220> FEATURE:
<221> NAME/KEY: MISC_FEATURE
<222> LOCATION: (19)..(19)
<223> OTHER INFORMATION: residue covalently linked to cysteamide

<400> SEQUENCE: 43

Xaa Leu Phe Leu Ala Arg Trp Arg Leu Leu Xaa Ser Leu Trp Xaa Leu
1               5                   10                  15

Leu Trp Lys

<210> SEQ ID NO 44
<211> LENGTH: 19
<212> TYPE: PRT
<213> ORGANISM: Artificial
<220> FEATURE:
<223> OTHER INFORMATION: synthesized peptide ST-VEPEP-6bb
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (11)..(11)
<223> OTHER INFORMATION: X = S, which is linked to the S residue at
      position 15 by a hydrocarbon linkage
<220> FEATURE:
<221> NAME/KEY: MISC_FEATURE
<222> LOCATION: (15)..(15)
<223> OTHER INFORMATION: X = S, which is linked to the S residue at
      position 11 by a hydrocarbon linkage
<220> FEATURE:
<221> NAME/KEY: MISC_FEATURE
<222> LOCATION: (19)..(19)
<223> OTHER INFORMATION: residue covalently linked to cysteamide

<400> SEQUENCE: 44

Xaa Leu Phe Arg Ala Leu Trp Arg Leu Leu Xaa Ser Leu Trp Xaa Leu
1               5                   10                  15

Leu Trp Lys

<210> SEQ ID NO 45
<211> LENGTH: 19
<212> TYPE: PRT
<213> ORGANISM: Artificial
<220> FEATURE:
<223> OTHER INFORMATION: synthesized peptide ST-VEPEP-6bd
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (11)..(11)
<223> OTHER INFORMATION: X = S, which is linked to the S residue at
      position 15 by a hydrocarbon linkage
<220> FEATURE:
<221> NAME/KEY: MISC_FEATURE
<222> LOCATION: (15)..(15)
<223> OTHER INFORMATION: X = S, which is linked to the S residue at
      position 11 by a hydrocarbon linkage
<220> FEATURE:
<221> NAME/KEY: MISC_FEATURE
```

```
<222> LOCATION: (19)..(19)
<223> OTHER INFORMATION: residue covalently linked to cysteamide

<400> SEQUENCE: 45

Xaa Leu Phe Leu Ala Arg Trp Arg Leu Leu Xaa Ser Leu Trp Xaa Leu
1               5                   10                  15

Leu Trp Lys

<210> SEQ ID NO 46
<211> LENGTH: 19
<212> TYPE: PRT
<213> ORGANISM: Artificial
<220> FEATURE:
<223> OTHER INFORMATION: synthesized peptide ST-VEPEP-6c
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (5)..(5)
<223> OTHER INFORMATION: X =  R, which is linked to the S residue at
      position 12 by a hydrocarbon linkage
<220> FEATURE:
<221> NAME/KEY: MISC_FEATURE
<222> LOCATION: (12)..(12)
<223> OTHER INFORMATION: X =  S, which is linked to the R residue at
      position 5 by a hydrocarbon linkage
<220> FEATURE:
<221> NAME/KEY: MISC_FEATURE
<222> LOCATION: (19)..(19)
<223> OTHER INFORMATION: residue covalently linked to cysteamide

<400> SEQUENCE: 46

Xaa Leu Phe Ala Xaa Leu Trp Arg Leu Leu Arg Xaa Leu Trp Arg Leu
1               5                   10                  15

Leu Trp Lys
```